United States Patent [19]

Box

[11] 4,221,870
[45] Sep. 9, 1980

[54] PROCESS FOR PRODUCING ANTIBIOTICS

[75] Inventor: Stephen J. Box, Plummers Plains, Near Horsham, England

[73] Assignee: Beecham Group Limited, England

[21] Appl. No.: 916,768

[22] Filed: Jun. 19, 1978

[30] Foreign Application Priority Data

Jul. 14, 1977 [GB] United Kingdom ............... 29569/77

[51] Int. Cl.² ............................................. C12P 17/18
[52] U.S. Cl. ..................................... 435/119; 435/886
[58] Field of Search ........................ 195/80 R; 435/119

[56] References Cited

U.S. PATENT DOCUMENTS 3,919,415 11/1975 Butterworth et al. ............. 195/80 R
3,928,569 12/1975 Umezawa et al. .................. 195/80 R

OTHER PUBLICATIONS

Hata et al., Journal of Antibiotics, vol. XXV, No. 8, pp. 473-474 (1972).
American Type Culture Collection Catalogue of Strains I, 12th Ed. p. 129 (1976).

*Primary Examiner*—Alvin E. Tanenholtz
*Attorney, Agent, or Firm*—Jacobs & Jacobs

[57] ABSTRACT

This invention provides a process for the preparation of salts of the β-lactamase inhibitory antibiotics MM4550A, MM13902 and MM17880, which are the compounds of the formulae (I)–(III), respectively:

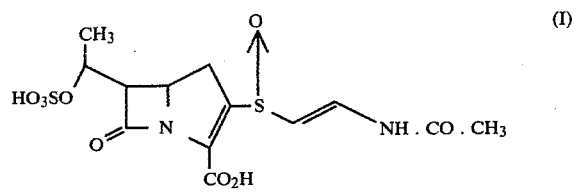

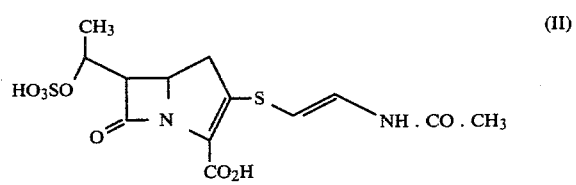

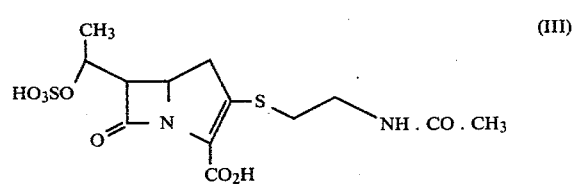

which process comprises cultivating a strain of *Streptomyces gedanensis* and isolating a salt of at least one of MM4550A, MM13902 and MM17880.

17 Claims, No Drawings

PROCESS FOR PRODUCING ANTIBIOTICS

The present invention relates to the production of β-lactamase inhibitory antibiotics and their salts.

The β-lactamase inhibitory antibiotics MM4550A, MM13902 and MM 17880 were disclosed in Belgian Patents Nos. 827331, 827332 and 839324 respectively MM 4550A, MM13902 and MM 17880 are now believed to be of the formula (I),(II) and (III) respectively:

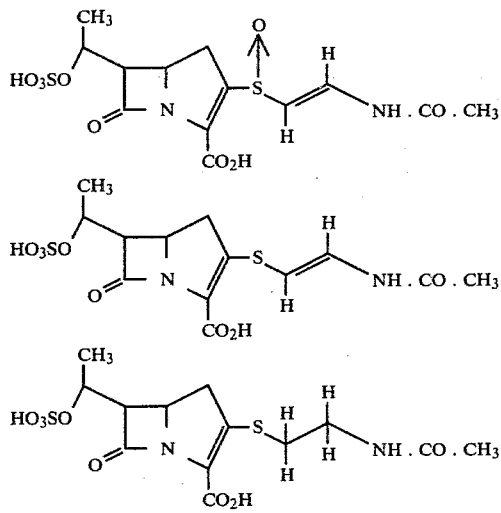

These compounds were described in Belgian Patents Nos. 827331, 827332 and 839324 as being produced during fermentation of strains of *Streptomyces olivaceus* and related organisms. *Streptomyces gedanensis* has been reported by Hata et al, *Journal of Antibiotics*, 25 , 473–4, 1972, as producing a high molecular weight β-lactamase inhibitor. The culture characteristics of *Streptomyces gedanensis* have been described by Waksman (The Actinomycetes Vol. 2, p. 216–217, Williams and Wilkins Co., Baltimore, U.S.A., 1961) and it has been deposited in the American Type Culture Collection as number 4880. *Streptomyces gedanensis* is not an organism that is related to *Streptomyces olivaceus* as described in Belgian Patents Nos. 827331, 827332 and 827324. It has now been found that MM 4550A, MM 13902 and MM 17880 are produced during the fermentation of *Streptomyces gedanensis*.

Accordingly the present invention provides a process for the preparation of a salt of at least one of MM 4550A, MM 13902 and MM 17880 which process comprises cultivation of a strain of *Streptomyces gedanensis* and recovering a salt of at least one of MM 4550A, MM 13902 1 and MM 17880, therefrom.

In one aspect the process is adapted to provide a salt of MM 4550A.

In a further aspect the process is adapted to provide a salt of MM 13902.

In a further aspect the process is adapted to provide a salt of MM 17880.

The process is suitably adapted to provide salts of at least two of MM 4550A, MM 13902 and MM 17880.

The process is more suitably adapted to provide salts of each of MM4550A, MM 13902 and MM 17880.

Most suitably the MM 4550A, MM 13902 or MM 17880 is recovered as a solid dibasic salt. Suitable salts include pharmaceutically acceptable salts, such as sodium, potassium, calcium, magnesium aluminium or conventional ammonium or substituted ammonium salts.

Preferably MM 4550A, MM 13902 or MM 17880 is recovered as a di-alkali metal salt such as a di-sodium or di-potassium salt.

Preferably *Streptomyces gedanensis* ATCC4880 or a high yielding mutant thereof is used in the process of this invention. *Streptomyces gedanensis* ATCC4880 has also been deposited at the CBS depositry at Baarn, the Netherlands.

When used herein, the term "cultivation" means the deliberate aerobic growth of *Streptomyces gedanensis* in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined. It has been found that media containing complex nutrients such as yeast extract, soya bean flour and the like are particularly suitable. It has also been found that the addition of cobalt ions is beneficial.

It has been found that cultivation at a temperature of $30\pm10°$ C. and preferably $26\pm4°$ C. gives acceptable yields of antibiotic and that a good time to harvest the broth is 1–7 days, and preferably 3–4 days, after the initiation of fermentation.

In general, all isolation and purification procedures used in obtaining the desired antibiotic should take place at non-elevated temperatures, for example, below 40° C. and preferably not above 12° C.

The desired product is normally obtained predominantly from the culture filtrate so that the preferred initial step in the isolation process is the removal of solid material from the fermentation, for example by filtration.

Impure preparations of salts of MM 4550, MM 13902 or MM 17880 may be obtained from the clarified culture filtrate by absorbing a salt of MM 4550A, MM 13902 or MM 17880 onto a material such as active carbon and then eluting with aqueous acetone and evaporating off the solvents under reduced pressure. The crude product from this process may be purified further by dissolving it in water and extracting into an organic phase using a lipophilic quaternary ammonium salt to form an organic solvent soluble salt followed by back extraction into water or dilute sodium iodide or the like.

Alternatively the culture filtrate may be extracted using a lipophilic quaternary ammonium salt and an organic solvent followed by the back extraction into an aqueous solution of an alkali metal iodide such as sodium iodide. This is frequently more effective than the preceding process.

It is believed that the chromatographic purification of salts of MM 4550A, MM 13902 and MM 17880 is best carried out using a salt of MM 4550A, MM 13902 and MM 17880 such as the sodium salt. Salts of MM 4550A, MM 13902 and MM 17880 are normally more soluble in aqueous and aqueous/alcohol solvent systems than in highly lipophilic solvents; consequently, it is preferred to use aqueous and aqueous/alcohol solvent systems in the chromatographic purifications used in this invention.

In our hands, aqueous solutions of electrolytes buffered to approximate neutrality have proved suitable for use in conjunction with polar support materials such as basic ion-exchange resins for the purification of MM 4550A MM 13902 1 and MM 17880. Thus an aqueous solution of sodium chloride buffered to about pH 7 with a conventional buffer such as phosphate buffer may be used in conjunction with support materials which contain quaternary ammonium groups. We have found that basic ion-exchange cross linked dextrans are suitable support materials and that QAE Sephadex A25 (Sephadex is a registered trademark) in particular is a highly suitable support material.

Separation of salts of MM 4550A, MM 13902 and MM 17880 from inorganic salts in particular but also from other contaminating substances may be achieved by adsorbing the antibiotic onto a lipophilic resin to which inorganic salts are not adsorbed. In our hands a polystyrene divinylbenzene co-polymer such as Amberlite XAD-4 is particularly suitable; the desired antibiotic may be removed from the column by elution (elution with water or aqueous alkanol) and the resulting solution concentrated by evaporation and freeze dried to yield a material of improved purity. Separation of salts of MM 4550, MM 13902 1 and MM 17880 from inorganic salts may also suitably be carried out by chromatography on a column composed of a gel-filtration agent, for example cross-linked dextran gels such as Sephadex G 15 and poly-acrylamide gels such as Biogel P2.

Further purification of MM 4550A, MM 13902 and MM 17880 from materials prepared using one or more of the processes described above may be carried out by column chromatography on an inert solid phase such as silica gel or cellulose using aqueous solvent systems. Suitable solvent systems will contain water and at least one lower alkanol, for example, water/isopropanol, water/n-propanol, water/methanol/isopropanol, water/butanol, water/ethanol/butanol or similar systems.

The salts of MM 4550A, MM 13902 and MM 17880 may be separated from each other by techniques described in the aforementioned Belgian Patents, or British Patents Nos: 1467413, 1489235 and 1483142 or U.S. Ser. Nos: 717917, 717334 and 717336, for example by chromatography on a basic ion-exchange cross linked dextran, such as QAE Sephadex A25, eluting with an aqueous solution of sodium chloride or column chromatography on cellulose eluting with an aqueous alcoholic solvent system, such as water/n-propanol or water/butanol/n-propanol.

The following examples are illustrative of the invention:

EXAMPLE 1

*Streptomyces gedanensis* ATCC 4880 was grown for 7 days at 26° C. on solid agar slants contained in McCartney bottles. The agar medium had the following composition:

|  | g/l |
|---|---|
| Yeast extract (Oxoid) | 4.0 |
| Malt Extract (Oxoid) | 10.0 |
| Dextrin | 4.0 |
| Bacto-Agar (Difco Ltd) | 20.0 |
| Demineralised water to 1 liter | |

(Oxoid Ltd., Wade Road, Basingstoke, Hants, U.K.; Dextrin is supplied by C.P.C. U.K. Ltd, Trafford Park, Manchester; Difco Laboratories, Detroit, Michigan, U.S.A.).

The medium was adjusted to pH 7.3 before sterilisation.

The medium was sterilised before inoculation by autoclaving for 15 minutes at 15 p.s.i. and 121° C.

The flasks were incubated on a rotary shaker (240 r.p.m. 1" throw) at 26° C. for 48 hours.

5 ml. portions of the seed stage were used to inoculate 100 ml portions of the fermentation of the media contained in 500 ml Ehrlenmeyer flasks closed with foam plastic plugs. The compositions of the fermentation media were as follows:

|  | g/l |
|---|---|
| Medium A | |
| Dextrin | 55.0 |
| Soya Bean flour | 20.0 |
| Mollasses | 20.0 |
| $NaH_2PO_4$ | 1.3 |
| KCl | 1.0 |
| deionised water to 1 liter. | |
| Medium B | |
| Malt extract | 10.0 |
| Bacteriological peptone | 10.0 |
| Glycerol | 20.0 |
| deionised water to 1 liter. | |

(The soya bean flour is Arkasoy 50 supplied by British Arkady Co., Old Trafford, Manchester, U.K.)

All fermentation media were sterilised before inoculation by autoclaving at 15 p.s.i. and 121° C. for 15 minutes.

The fermentation flasks were incubated at 26° C. on a rotary shaker at 240 r.p.m. with 1" throw. 5 ml. samples were withdrawn from the flasks using sterile technique on days 3 to 7 inclusive of the fermentation. The samples were centrifuged at 2,200 g. for 10 minutes; the resulting supernatant was used for the assay of biological activity. The samples were assayed using the hole in plate method on:

(a) agar plates seeded with *Klebsiella aerogenes* NCTC 418

(b) agar plates containing penicillin G seeded with *Klebsiella aerogenes* NCTC 418. The level of activity was measured by the KAG system described in Belgian Patent No. 827331.

The level of activity on the KAG system also included measurement against a standard preparation of MM4550 and the results on this system are expressed both as zone diameters of inhibition and μg/ml of MM4550A.

| Length of Fermentation (days) | Activity on Klebsiella a NCTC 418 Zone diam. (mm) | Activity on KAG Zone diam. (mm) | Activity on KAG as 4550A μg/ml |
|---|---|---|---|
| Medium A | | | |
| 3 | NA | 20.2 | <0.15 |
| 4 | 19.2 | 25.2* | 0.3 |
| 5 | 17.9 | 32.5 | 0.8 |
| 6 | 17.5 | 29.4 | 0.74 |
| 7 | 14.6 | 28.6 | 0.27 |
| Medium B | | | |
| 3 | NA | NA | |
| 4 | NA | 19.1 | <0.15 |
| 5 | NA | 22.0 | <0.15 |
| 6 | NA | 16.3 | <0.15 |

-continued

| Length of Fermentation (days) | Activity on Klebsiella a NCTC 418 Zone diam. (mm) | Activity on KAG Zone diam. (mm) | Activity on KAG as 4550A μg/ml |
|---|---|---|---|
| 7 | NA | 18.2 | <0.15 |

NA = not active
*sample assay at 1 in 2 dilution

10 μl samples of the culture filtrate harvested on day 6 of the fermentation in medium A were spotted on 1 cm wide strips of Whatman No. 1 chromatography paper. These strips were chromatographed overnight at 4° C. in the following solvent system:

Butanol:acetic acid:water 12:3:5

Authentic samples of disodium MM4550A were also chromatographed in the same system as markers.

The tapes were dried and laid on agar plates containing penicillin G seeded with *Klebsiella aerogenes NCTC 418* (KAG plates). After incubation of the plates at 40° C. for 6 hours zones of inhibition of growth were seen. The $R_f$'s of the zones are tabulated.

| Sample | $R_f$ |
|---|---|
| Culture filtrate | 0.16 |
| MM4550 Na$_2$ salt | 0.16 |

EXAMPLE 2

*Streptomyces gedanensis* ATCC 4880 was grown for 7 days at 28° C. on solid agar slants contained in Roux bottles. The agar medium had the following composition:

| | g/l |
|---|---|
| Yeast extract (oxoid) | 4.0 |
| Malt extract (oxoid) | 10.0 |
| Dextrin | 4.0 |
| Bacto-Agar (Difco Ltd.) | 20.0 |
| Demineralised water to 1 liter | |

(Oxoid Ltd., Wade Road, Basingstoke, Hants, U.K.; Dextrin is supplied by C.P.C. (U.K.) Ltd., Trafford Park, Manchester; Difco Laboratories, Detroit, Michigan, U.S.A.).

The medium was adjusted to pH 7.3 before sterilisation. 50 ml of sterile deionised water containing 0.05% Triton X (registered Trademark) was added to one Roux bottle and a suspension of spores and mycelium produced by scraping the surface of the culture sterile technique. 10 ml portions of the suspension were used as inoculum for 500 ml aliquots of the seed stage contained in 2 liter Ehrlenmeyer flasks closed with cotton wool plugs.

The seed stage medium had the following composition:

| | g/l |
|---|---|
| Dextrin | 20.0 |
| Yeatex | 10.0 |
| NaCl | 5.0 |
| KH$_2$PO$_4$ | 5.0 |
| Demineralised water to 1 liter | |

(Yeatex is yeast extract supplied by Bovril Foods Ltd., PO. Box 18, Wellington Road, Burton on Trent).

The medium was adjusted to pH 7 and steam sterilised at 121° C. for 15 minutes. The seed stage flasks, after inoculation were incubated at 28° C. on a gyratory shaker at 240 r.p.m. with 2″ throw. After 64 hours incubation 4 liters of the seed stage were used to inoculate 150 liters of the fermentation medium contained in a 300 liter fully baffled stainless steel fermenter.

The fermentation medium had the following compositions:

| | g/l |
|---|---|
| Glycerol | 30 ml |
| Soya bean flour | 10.0 |
| CaCO$_3$ | 0.2 |
| Na$_2$SO$_4$ | 0.5 |
| CoCl$_2$ 6H$_2$O | 0.001 |
| Antifoam | 1 ml |
| Tap water to 1 liter | |

The antifoaming agent consisted of a 10% solution of Pluronic L81 (Ugine Kuhlmann Chemicals Ltd) dispersed in Soyabean oil (British Oil & Cake Mills Ltd).

(The soya bean flour is Arkasoy '50' supplied by the British Arkady Co. Ltd., Old Trafford, Manchester).

The fermentation medium was steam sterilsed in the fermenter for 20 minutes at 120° C.

The fermentation was agitated using an 8½″ diameter vaned disc impeller which was driven at 340 r.p.m., sterile air was supplied at 50 liters/minute and the temperature maintained at 26° C. Further additions of the antifoam agent were made as required during the fermentation to control foaming. The fermentation was harvested after 72 hours when the titre of MM4550A hd reached 9.6 μg/ml as estimated using the standard hole in plate agar diffusion bioassay technique on the KAG plate system (described in Belgian Patent No.: 827331).

The whole brew was clarified by centrifugation. The clarified brew (135 liters) was extracted at 15° C. with dichloromethane (44 litres) containing cetyl dimethylbenzyl ammonium chloride (110 g) by pumping the two liquids at predetermined flow rates, 4.5 liters/min. and 900 ml/min. respectively, through an in-line mixer. The phases were separated in a continuous centrifuge having been admixed for about 2 minutes. The dichloromethane phase was back extracted with 1/50 volume of a 3% aqueous sodium iodide solution; the phases were separated by centrifugation. The back extract was assayed using a β-lactamase inhibition assay such as that described in Belgian Patent No: 827331 giving a level of about 180–190 μg/ml. of MM4550A. The extract was adjusted to pH 6.9, filtered through a bed of filter aid (dicalite) and freeze dried to yield a solid (8.6 g.).

The freeze dried solid was washed with acetone (600 ml), and the washings discarded. The remaining solid was dissolved in distilled water (100 ml) and run onto a QAE Sephadex A25 column (3.8×30 cm) (QAE Sephadex is supplied by Pharmacia Ltd.) equilibrated in 0.22 M aqueous NaCl (pH 7). The column was eluted with 0.22 M aqueous NaCl (1350 ml) at 5 ml/min. and at 5° C. 15 ml. fractions were collected. The column was further eluted, under the same conditions with 0.8 M aqueous NaCl (2100 ml). The fractions were monitored for their UV spectra and activity in a β-lactamase inhibition assay. Fractions (100–140) showing the highest levels of β-lactamase inhibition were combined. The combined fractions were evaporated under reduced pressure to approximately 10 ml volume.

A Biogel P2 (200–400 mesh) column (3.8×40 cm) (supplied by Bio Rad Laboratories) was prepared in 1% butanol. The concentrate from the QAE Sephadex column was loaded onto the gel column and the column eluted with 1% butanol at a flow rate of 2 ml/minute and at 5° C. 5 ml fractions were collected. Fractions (43–45) gave UV spectra described in Belgian Patent No. 827331 as being characteristic of MM4550A and gave high levels of β-lactamase inhibition on a β-lactamase inhibition assay. These fractions were combined and freeze dried to yield a solid (14 mg) with a UV spectrum characteristic of MM4550A.

This solid was dissolved at 200 μg/ml in distilled water and spotted at 5 μg/origin on 1 cm wide strips of Whatman No: 1 chromatography paper. These strips were chromatographed for 16 hours at 4° C. in three solvent systems. The tapes were dried and laid on agar plates seeded with *Klebsiella aerogenes* NCTC 418 and containing penicillin G (KAG plates). After incubation of the plates for 7 hours at 40° C. zones of inhibition of growth were seen. The $R_f$'s of these zones and those of an authentic sample of MM4550A chromatographed at the same time are shown in table 1.

Table 1
$R_f$ values of active component obtained from
S. gedanensis and disodium MM4550A in different solvent systems.

| Solvent System | $R_f$ of active component from S. gedanensis | $R_f$ of MM4550A Na2 salt |
|---|---|---|
| Butanol:ethanol:water (4:1:5 top phase) | 0.03 | 0.03 |
| Butanol:acetic acid:water (12:3:5) | 0.17 | 0.17 |
| Butanol:pyridine:water (1:1:1) | 0.50 | 0.50 |

EXAMPLE 3

*Streptomyces gedanensis* ATCC 4880 was grown for seven days on solid agar slants contained in McCartney bottles. The composition of the medium was:

| | g/l |
|---|---|
| Yeast extract (Oxoid) | 4.0 |
| Malt extract (Oxoid) | 10.0 |
| Dextrin | 4.0 |
| Bacto-agar (Difco) | 20.0 |
| Demineralised water to 1 liter. | |

(Difco Laboratories, Detroit, Michigan, U.S.A.)
(Oxoid Limited, Wade Road, Basingstoke, Hants, U.K.)
(Dextrin is supplied by C.P.C. (U.K.) Ltd, Trafford Park, Manchester. U.K.)

The medium was adjusted to pH 7.3 before sterilisation.

Growth scraped from slants was used directly to inoculate 100 ml portions of the seed stage medium contained in 500 ml Ehrlenmeyer flasks closed with foam plastic plugs. The composition of the seed medium was:

| | g/l |
|---|---|
| Dextrin | 20.0 |
| Yeatex | 10.0 |
| NaCl | 5.0 |
| KH2PO4 | 5.0 |
| Deionised water to 1 liter | |

The medium was adjusted to pH 7 before sterilisation (Yeatex is Yeast extract supplied by Bovril Foods Limited., P.O Box 18, Wellington Road, Burton on Trent.)

The medium was sterilised before inoculation by autoclaving for 15 minutes at 15 p.s.i. and 121° C. The seed stage flasks after inoculation were incubated at 26° C. on a rotary shaker (240 r.p.m. at 1" throw) for 48 hours.

5 ml portions of the seed stage were used to inoculate 100 ml portions of the fermentation medium contained in 500 ml Ehrlenmeyer flasks closed with foam plastic plugs. The composition of the fermentation medium was as follows:

| | g/l |
|---|---|
| Glycerol | 30.0 |
| Soya Bean Flour | 10.0 |
| CaCO3 | 0.2 |
| Na2SO4 | 0.5 |
| CoCl2 6H2O | 0.01 |
| Deionised water to 1 liter. | |

(The soya bean flour is Arakasoy "50" supplied by the British Arkady Co., Old Trafford, Manchester, U.K.)

The medium was sterilised before inoculation by autoclaving for 15 minutes at 15 p.s.i. and 121° C.

The fermentation flasks were incubated at 26° C. on a rotary shaker (240 r.p.m. 1" throw) for 96 hours. The flasks were harvested and centrifuged at 2,200 g for 10 minutes. The resulting culture filtrate (370 ml, pH 6.3) was shaken with dichloromethane (100 ml) containing cetyldimethylbenzyl-ammonium chloride (300 mg). The phases were separated and the dichloromethane phase extracted with a 0.3% aqueous sodium iodide solution (100 ml). The phases were separated and the aqueous phase retained. The aqueous phase was evaporated under reduced pressure to remove any residual dichloromethane and freeze dried. The freeze dried solid was washed twice with acetone and the washings discarded. The remaining solid (18 mg) was submitted to high pressure liquid chromatography.

The chromatographic column C18μ Bondapak (0.64×30 cm) (Supplied by Waters Associates Ltd, Vauxhall Works, Greg Street, Reddish, Stockport, U.K.) equilibrated in 0.04 M ammonium acetate containing 5% acetonitrile (pH 4.5). The solid from the extraction was dissolved in deionised water (10 mg/ml). Insoluble material was removed by filtration through a filter with 0.22μ pore size (Millipore (U.K.) Ltd, Wembley, Middlesex, U.K.).

A 25 μl sample of the filtrate was injected onto the top of the column. The column was eluted with 0.4 M ammonium acetate containing 5% acetonitrile (pH 4.5) at a flow rate of 1 ml/minute. The eluate from the column was continuously monitored, using a spectrophotometer with flow cell, at 298 nm the full scale deflection was 0.1 absorbance units. There was a peak in U.V. absoption for the eluate having a retention time of 30.5 minutes. Fractions were also collected from the column and the biological activity of these fractions measured by dipping 6 mm diameter Whatman Antibiotic assay discs (W. R. Balston, Maidstone, Kent, U.K.) in the fraction, drying the disc and plating on a KAG bioassay plate. The fraction collected between 29.75 and 30.75 minutes retention time on the column had activity on the KAG system.

An authentic sample of disodium MM13902 run on the same column under the same conditions had a retention time of 30.5 minutes.

EXAMPLE 4 *Streptomyces gedanensis* ATCC 4880 was grown for 7 days at 28° C. on solid agar slants contained in McCartney bottles. The composition of the medium was:

|  | g/l |
| --- | --- |
| Yeast extract (Oxoid) | 4.0 |
| Malt extract (Oxoid) | 10.0 |
| Dextrin | 4.0 |
| Bacto-agar (Difco) | 20.0 |
| Demineralised water to 1 liter. | |

(Difco Laboratories, Detroit, Michigan, U.S.A.)
(Oxoid Limited, Wade Road, Basingstroke, Hants, U.K.)
(Dextrin is supplied by C.P.C. (U.K.) Ltd, Trafford Part, Manchester, U.K.)

The medium was adjusted to pH 7.3 before sterilisation.

Growth scraped from slants was used directly to inoculate 100 ml portions of the seed stage medium contained in 500 ml Ehrlenmeyer flasks closed with foam plastic plugs. The composition of the seed medium was:

|  | g/l |
| --- | --- |
| Dextrin | 20.0 |
| Yeatex | 10.0 |
| NaCl | 5.0 |
| KH$_2$PO$_4$ | 5.0 |
| Deionised water to 1 liter | |

The medium was adjusted to pH 7 before sterilisation (Yeatex is Yeast extract supplied by Bovril Foods Limited, P.O. Box 18, Wellington Road, Burton on Trent.)

The medium was sterilised before inoculation by autoclaving for 15 minutes at 15 p.s.i. and 121° C. The seed stage flasks after inoculation were incubated at 26° C. on a rotary shaker. (240 r.p.m. at 1" throw) for 48 hours.

5 ml portions of the seed stage were used to inoculate 100 ml portions of the fermentation medium contained in 500 ml Ehrlenmeyer flasks closed with foam plastic plugs. The composition of the fermentation medium was as follows:

|  | g/l |
| --- | --- |
| Glycerol | 30.0 |
| Soya Bean Flour | 10.0 |
| CaCO$_3$ | 0.2 |
| Na$_2$SO$_4$ | 0.5 |
| CoCl$_2$6H$_2$O | 0.01 |
| Deionised water to 1 liter. | |

(The soya bean flour is Arakasoy "50" supplied by the British Arkady Co., Old Trafford, Manchester, U.K.)

The medium was sterilised before inoculation by autoclaving for 15 minutes at 15 p.s.i. and 121° C.

The fermentation flasks were incubated at 26° C. on a rotary shaker (240 r.p.m. 1" throw) for 96 hours. The flasks were harvested and centrifuged at 2,200 g for 10 minutes. The resulting culture filtrate (370 ml, pH 6.3) was shaken with dichloromethane (100 ml) containing cetyldimethylbenzyl-ammonium chloride (300 mg). The phases were separated and the dichloromethane phase extracted with a 0.3% aqueous sodium iodide solution (100 ml). The phases were separated and the aqueous phase retained. The aqueous phase was evaporated under reduced pressure to remove any residual dichloromethane and freeze dried. The freeze dried solid was washed twice with acetone and the washings discarded. The remaining solid (18 mg) was submitted to high pressure liquid chromatography.

The chromatographic column was C$_{18}\mu$ Bondapak (0.64×30 cm) (Supplied by Waters Associates Ltd, Vauxhall Works, Greg Street, Reddish, Stockport, U.K.) equilibrated in 0.04 M ammonium acetate containing 5% acetonitrile (pH 4.5). The solid from the extraction was dissolved in deionised water (10 mg/ml). Insoluble material was removed by filtration through a filter with 0.22$\mu$ pore size (Millipore (U.K.) Ltd, Wembley, Middlesex, U.K.).

A 25 $\mu$l sample of the filtrate was injected onto the top of the column. The column was eluted with 0.4 M ammonium acetate containing 5% acetonitrile (pH 4.5) at a flow rate of 1 ml/minute. The eluate from the column was continuously monitored, using a spectrophotometer with flow cell, at 298 mm, the full scale deflection was 0.1 absorbance units. A peak of UV absorption was eluted from the column at a retention time of 12.25 minutes Fractions were also collected from the column and the biological activity of these fractions measured by dipping 6 mm diameter Whatman Antibiotic assay discs. (W. R. Balston, Maidstone, Kent, U.K.) in the fraction, drying the disc and plating on a KAG bioassay plate. The fraction collected between 11.74 and 12.75 minutes retention time on the column had activity on the KAG system.

An authentic sample of disodium MM17880 run on the same column under the same conditions had a retention time of 12.75 minutes.

What we claim is:

1. A process for the preparation of a salt at least one of MM4550A, MM13902 and MM17880, which process comprises cultivating a strain of *Streptomyces gedanensis* in the presence of assimilable souces of carbon, nitrogen, sulphur and mineral salts and isolating a salt of at least one of MM4550A, MM13902 and MM17880.

2. A process according to claim 1 wherein a salt of MM4550A is isolated.

3. A process according to claim 1 wherein a salt of MM13902 is isolated.

4. A process according to claim 1 wherein a salt of MM17880 is isolated.

5. A process according to claim 1 wherein salts of at least two of MM4550A, MM13902 and MM17880 are isolated.

6. A process according to claim 1 wherein salts of each of MM4550A, MM13902 and MM17880 are isolated.

7. A process according to claim 1 wherein the salts of MM4550A, MM13902 and MM17880 is isolated as a solid dibasic salt.

8. A process according to claim 7 wherein the salt is a pharmaceutically acceptable salt.

9. A process according to claim 8 wherein the salt is a sodium, potassium, calcium, magnesium, aluminium, ammonium or substituted ammonium salt.

10. A process according to claim 9 wherein the salt is the di-sodium or di-potassium salt.

11. A process according to claim 1 wherein the strain of *Streptomyces gedanensis* is *Steptomyces gedanensis* ATCC 4880 or a high yielding mutant thereof.

12. A process according to claim 1 which further comprises partial purification of the salt of MM4550A, MM13902 and MM17880 by absorbing the salt onto active carbon and eluting with aqueous acetone.

13. A process according to claim 1 which further comprises purification of the salt of MM4550A, MM13902 and MM17880 by extraction with a lipophilic quaternary ammonium salt and an organic solvent, followed by back extraction into an aqueous solution of an alkali metal iodide.

14. A process according to claim 1 which further comprises purification of the salt of MM4550A, MM13902 and MM17880 by chromatography on a basic ion exchange resin and elution with aqueous sodium chloride solution.

15. A process according to claim 1 which further comprises purification of the salt of MM4550A, MM13902 and MM17880 by absorbing the salt on a lipophilic resin and eluting with water or aqueous alkanol.

16. A process according to claim 1 which further comprises purification of the salt of MM4550A, MM13902 and MM17880 by chromatography on silica gel or cellulose using an aqueous alkanol solvent system.

17. A process according to claim 1 which further comprises purifying the salt of MM4550A, MM13902 by chromatography on a basic ion-exchange cross-linked dextran and eluting with an aqueous solution of sodium chloride.

* * * * *